(12) United States Patent
Black et al.

(10) Patent No.: US 8,475,759 B2
(45) Date of Patent: Jul. 2, 2013

(54) EFFERVESCENT COMPOSITION FOR IMPROVED CARBON DIOXIDE GENERATION IN INSECT MONITOR DEVICES

(75) Inventors: Bruce C. Black, Yardley, PA (US); Shreya Sheth, Levittown, PA (US); Linda Varanyak, Mercerville, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 13/253,136

(22) Filed: Oct. 5, 2011

(65) Prior Publication Data

US 2012/0141353 A1 Jun. 7, 2012

Related U.S. Application Data

(60) Provisional application No. 61/458,935, filed on Dec. 3, 2010.

(51) Int. Cl.
*C01B 31/20* (2006.01)
*A01M 1/02* (2006.01)
*A01M 1/20* (2006.01)

(52) U.S. Cl.
USPC ............... 423/438; 423/437.1; 423/419.1; 43/107; 43/122; 43/123; 252/4; 252/5; 252/183.11; 252/183.12; 252/183.13; 510/116; 510/117

(58) Field of Classification Search
USPC ............ 423/437.1, 419.1, 438; 43/107, 122, 43/123; 252/4, 5, 6, 183.11, 183.12, 183.13; 510/116, 117
See application file for complete search history.

(56) References Cited

U.S. PATENT DOCUMENTS

| | | | |
|---|---|---|---|
| 3,888,976 A * | 6/1975 | Mlkvy et al. | 424/44 |
| 4,506,473 A | 3/1985 | Waters, Jr. | |
| 4,552,679 A * | 11/1985 | Schobel et al. | 510/117 |
| 4,671,972 A * | 6/1987 | Schobel et al. | 427/213 |
| 5,736,158 A * | 4/1998 | Quast | 424/464 |
| 6,055,766 A | 5/2000 | Nolen et al. | |
| 6,468,950 B1 * | 10/2002 | Kawasaki et al. | 510/116 |
| 6,566,392 B1 * | 5/2003 | Okada et al. | 514/461 |
| 6,605,583 B1 * | 8/2003 | Gorlin | 510/314 |
| 6,610,206 B1 * | 8/2003 | Callan et al. | 210/646 |
| 6,858,139 B2 * | 2/2005 | Taylor | 210/232 |
| 6,920,716 B2 | 7/2005 | Kollars, Jr. et al. | |
| 7,165,353 B2 | 1/2007 | Matts et al. | |
| 2007/0148112 A1 * | 6/2007 | Dingley et al. | 424/63 |
| 2008/0148624 A1 | 6/2008 | Borth et al. | |
| 2009/0145019 A1 | 6/2009 | Nolen et al. | |
| 2009/0145020 A1 | 6/2009 | McKnight | |
| 2011/0044936 A1 * | 2/2011 | Black et al. | 424/84 |
| 2012/0110894 A1 * | 5/2012 | Black et al. | 43/123 |

FOREIGN PATENT DOCUMENTS

KR 1020070067762 A 6/2007

* cited by examiner

*Primary Examiner* — Joseph D Anthony
(74) *Attorney, Agent, or Firm* — FMC Corporation

(57) ABSTRACT

The present invention relates to a chemical composition and method of generating carbon dioxide for use with an insect monitor and/or capture device comprising:
i) an effervescent agent;
ii) a solid acid;
iii) a deliquescent agent; and optionally
iv) an anti-clumping agent.

8 Claims, No Drawings

EFFERVESCENT COMPOSITION FOR IMPROVED CARBON DIOXIDE GENERATION IN INSECT MONITOR DEVICES

CROSS-REFERENCE TO RELATED APPLICATIONS

This application claims the benefit of U.S. Provisional Application No. 61/458,935 filed Dec. 3, 2010.

FIELD OF THE INVENTION

The present invention relates to chemical compositions which regulate the generation of carbon dioxide useful for attracting insects to an insect monitor and/or capture device.

BACKGROUND OF THE INVENTION

Bed bugs are small nocturnal insects of the family Cimicidae that feed off the blood of humans and other warm blooded hosts. Bed bugs exhibit cryptic behavior, which makes their detection and control difficult and time consuming. This is particularly true for the common bedbug, Cimex lectularius, which has become well adapted to human environments. Other species of bed bugs are nuisances to people and/or animals as well.

While bed bugs have been controlled in many areas, such as the United States, the increase in international travel has contributed to a resurgence of these pests in recent years. There are many aspects of bed bugs which make it difficult to eradicate them once they have established a presence in a location. Accordingly, there is a need for effective traps to determine the presence of bed bugs before they become entrenched.

Adult bed bugs are about 6 millimeters long, 5 to 6 millimeters wide, and are reddish brown with oval, flattened bodies. The immature nymphs are similar in appearance to the adults, but are smaller and lighter in color. Bed bugs do not fly, but can move quickly over surfaces. Female bed bugs lay their eggs in secluded areas and can deposit up to five eggs per day, and as many as 500 during a lifetime. The bed bug eggs are very small, about the size of a dust spec. When first laid, the eggs are sticky causing them to adhere to surfaces.

Bed bugs can go for long periods of time without feeding. Nymphs can survive for weeks without feeding, while adults can survive for months.
Consequently, infestations cannot be eliminated simply by leaving a location unoccupied for brief periods of time.

While bed bugs are active during the nighttime, during daylight they tend to hide in tiny crevices or cracks. Bed bugs may therefore find easy hiding places in beds, bed frames, furniture, along baseboards, in carpeting and countless other places. Bed bugs tend to aggregate but do not build nests like some other insects.

Bed bugs obtain their sustenance by drawing blood through elongated mouth parts. They may feed on a human for 3 to 10 minutes, although the person is not likely to feel the bite. After the bite, the victim often experiences an itchy welt or a delayed hypersensitivity reaction resulting in a swelling in the area of the bite. However, some people do not have any reaction or only a very small reaction to a bedbug bite. Bed bug bites have symptoms that are similar to other pests, such as mosquitoes and ticks. It is not possible to determine whether a bite is from a bed bug or another type of pest; and bites may be misdiagnosed as hives or a skin rash. Consequently, bed bug infestations may frequently go on for long periods before they are recognized.

Bed bug infestations originate by a bed bug being carried into a new area. Bed bugs are able to cling to possessions and hide in small spaces, such that they may be transported in a traveler's belongings. As a result, buildings where the turnover of occupants is high, such as hotels, motels, inns, barracks, cruise ships, shelters, nursing homes, camp dwellings, dormitories, condominiums and apartments, are especially vulnerable to bed bug infestations.

Because of all the features of bed bugs described herein, bed bugs are both difficult to detect and eradicate. Professional pest removal specialists and pesticides are needed. It is necessary to remove all clutter and unnecessary objects from a room, remove bed bugs and eggs as much as possible through vacuuming, and apply pesticides to likely hiding areas. This type of treatment for eradication can be disruptive to a business such as a hotel. As a result, it is desirable to detect bed bug infestations as early as possible in order to begin eradication procedures.

The tiny, mobile and secretive behavior of bed bugs makes it nearly impossible to prevent and control an infestation unless they are quickly discovered and treated. Bed bugs have been found to move through holes in walls, ceilings and floors into adjacent rooms. Devices and methods for the early detection of bed bugs are especially needed in the hospitality industries.

While several attempts have been made to devise bed bug monitoring and/or capture devices in the past, these devices have, in general, not proven to be commercially effective. The present inventors have studied many aspects of bed bug behavior, and believe that one factor in the failure of such devices to desirably perform is the lack of an effective lure to attract bed bugs to the trapping mechanism.

Research has shown that carbon dioxide alone is an effective attractant to lure bed bugs to monitors and traps. Carbon dioxide can also be used with additional chemical attractants, to further enhance the effectiveness of the lures. There are a few carbon dioxide producing monitors commercially available which use pressurized carbon dioxide canisters, dry ice or yeast fermentation to generate carbon dioxide. The technology involved in delivering compressed carbon dioxide safely into a monitor is expensive. While dry ice is relatively inexpensive, it can be dangerous to handle, not convenient to purchase and only lasts for a few hours. Although generation of carbon dioxide by yeast fermentation is economical and safe, the preparation procedure requires mixing carefully measured amounts of yeast, media and water at a temperature of 20° C. to 30° C. in a separate carbon dioxide generation container which, if spilled, would be unpleasant to clean up.

It is well known in the art that certain acid base chemical reactions can generate carbon dioxide. For example, the reaction of citric acid with sodium bicarbonate in an aqueous medium produces carbon dioxide, however this reaction is relatively quick and the carbon dioxide is generated within minutes. Commercial products such as Alka-Seltzer® and Bromo-Seltzer® are examples of the fast reaction of citric acid and sodium bicarbonate when placed into water. In order to be useful in attracting insects to a monitor or capture device, carbon dioxide should be generated slowly for prolonged periods of time.

The present invention overcomes the above-identified problems by providing a long lasting carbon dioxide generating chemical composition using environmentally safe, non-toxic ingredients, without the addition of water, to economically produce a sufficient amount of carbon dioxide for a prolonged period of time in order to aid in attracting bed bugs to bed bug monitors and/or capture devices.

SUMMARY OF THE INVENTION

The present invention relates to a chemical composition and method of carbon dioxide generation for use with an insect monitor and/or capture device comprising:
i) an effervescent agent,
ii) a solid acid;
iii) a deliquescent agent, and optionally
iv) an anti-clumping agent.

DETAILED DESCRIPTION OF THE INVENTION

The present invention relates to a chemical composition and method of carbon dioxide generation for use with an insect monitor and/or capture device comprising:
i) an effervescent agent,
ii) a solid acid;
iii) a deliquescent agent, and optionally
iv) an anti-clumping agent.
Another embodiment of the present invention is a method of generating carbon dioxide for use with an insect monitor and/or capture device comprising the combination of:
i) an effervescent agent,
ii) a solid acid;
iii) a deliquescent agent, and optionally
iv) an anti-clumping agent.
in the presence of at least 11% relative humidity.

The effervescent agent can be, for example, an alkaline carbonate salt or a combination of alkaline carbonate salts such as sodium carbonate, sodium bicarbonate, potassium carbonate, potassium bicarbonate, ammonium carbonate, ammonium bicarbonate and calcium carbonate. The preferred effervescent agent is sodium bicarbonate.

Solid acids usable in the present invention include, for example, citric acid monohydrate, maleic acid, malic acid, oxalic acid, malonic acid, tartaric acid, aspartic acid, fumaric acid, isophthalic acid, phthalic acid, terephthalic acid, salicylic acid, gentisic acid, gallic acid, mandelic acid, tropic acid, cinnamic acid, benzoic acid, nicotinic acid, phenylacetic acid, sorbic acid, 2-pyrrolidone-5-carboxylic acid, trimellitic acid, p-toluene sulfonic acid and benzene sulfonic acid. The preferred solid acid is citric acid monohydrate. An anti-clumping agent, such as fumed silica, for example, Cab-O-Sil® Fumed Silica available from Cabot Corporation, amorphous silica, for example Siloid® Silica available from W.R. Grace and Company, kaolin clay, or mixtures thereof, can be added to the solid acid to maintain a free flowing dry material while in storage. The anti-clumping agent is preferably a 1:1 mixture of fumed silica and amorphous silica present in an amount of about 5% by weight to the dry acid.

The deliquescent agent, can be, for example, a hydrated metal salt selected from the group consisting of magnesium chloride hexahydrate, magnesium bromide hexahydrate, aluminum chloride hexahydrate, aluminum fluoride trihydrate, calcium chloride hexahydrate, iron(II) chloride tetrahydrate, iron(II) nitrate nonahydrate, magnesium nitrate hexahydrate and aluminum nitrate nonahydrate.

The reaction between the solid acid and effervescent agent is an acid base reaction. For example, the reaction between citric acid and sodium bicarbonate produces water, carbon dioxide, sodium hydrogen citrate, and sodium citrate. Normally this acid base reaction would take place in an aqueous medium, however the aqueous reaction is rather quick and the carbon dioxide is released within minutes. The inventors have found that the addition of a deliquescent agent to an effervescent agent and a solid acid promotes the acid base reaction and slowly maintains the reaction by drawing water from the atmosphere to supplement the water generated in the reaction.

In order to sustain the acid base reaction and produce carbon dioxide at a slow and sustainable rate for prolonged periods of time, the molar ratio of the effervescent agent to solid acid to deliquescent agent can be adjusted. A sufficient amount carbon dioxide flow rate in order to attract bed bugs is about 0.5 mL/minute. It is believed that higher carbon dioxide flow rates will result in an increase in bed bug attraction. A sufficient amount of carbon dioxide can be generated using a mixture of sodium bicarbonate, citric acid monohydrate and magnesium chloride hexahydrate, without further addition of water, wherein the molar ratio of the effervescent agent to solid acid to deliquescent agent is from 159:52:1 to 10:3:1, in the presence of at least 11% relative humidity. The preferred molar ratio of the effervescent agent to solid acid to deliquescent agent is from 40:13:1 to 20:6.5:1.

The present invention therefore provides an environmentally safe, nontoxic carbon dioxide generating chemical composition, and a method of using the composition, to economically produce sufficient amounts of carbon dioxide for a prolonged period of time in order to aid in attracting insects, such as bed bugs, to insect monitors and/or capture devices. The water necessary for the chemical composition to generate carbon dioxide is derived from the humidity in the surrounding atmosphere, eliminating the need to measure and add water to initiate and sustain the acid base reaction. An additional benefit of the present invention is that the by-products are 100% biodegradable and can be disposed of easily.

The present composition can be used alone to attract insects such a bed bugs to a monitor and/or capture device or in combination with other insect attractants. Attractants which may be employed include heat, pheromones, human sweat components and the like, all of which are known to those of skill in the art. Mixtures of one or more attractants may also be employed.

One attractant which is particularly preferred is a composition comprising an unsaturated aldehyde component and an organic acid component. It is preferred that the unsaturated aldehyde component be comprised of one or more aldehyde selected from the group consisting of trans-2-hexen-1-al (Hexenal) and trans-2-octen-1-al (Octenal). It is preferred that the organic acid component be butyric acid. When the aldehyde component is comprised of both Hexenal and Octenal, it is preferred that the aldehydes be present in a ratio of from about 1:5 and about 5:1 of Hexenal to Octenal, more preferably in a ratio of between about 3:1 and about 1:3. In order to be most attractive to bed bugs, the optimal concentration of the Hexenal and Octenal mixture to be released is from about 300 ng/hr to about 500 ng/hour, and the optimal concentration of butyric acid to be released is between about 100 ng/hr and about 300 ng/hr. Mixing butyric acid with Hexenal and Octenal forms an unstable composition and it is necessary to separate the aldehyde component from the acid component. In order for the separate components of the attractant composition to be released at the proper rates, each component may be incorporated into a formulation which can be in gel form, a solid form, dissolved in a polar solvent such as water, dissolved in an organic solvent, for example a $C_8$-$C_{12}$ alkane, and preferably a $C_9$-$C_{10}$ alkane, encapsulated, or impregnated into other materials. In one aspect of the invention suitable attractants comprise Octenal dissolved in decane at a concentration range of about 2000 to 3000 ppm Octenal, preferably from about 2500 to 2800 ppm Octenal, and more preferably from about 2700 to 2750 ppm Octenal. A second suitable attractant that can be used in conjunction with the Octenal is butyric acid dissolved in decane at a concentration range of about 200 to 2000 ppm butyric acid, and preferably from about 240 to 400 ppm butyric acid.

Each component may be incorporated into an absorbent material, for example, but not limited to, cotton batting, fiberised cellulose wood pulp, synthetic batting, polyester batting, felt, bonded carded webs, very high density polyethylene sponge and high loft spunbond materials. In order to regulate diffusion, a semi-permeable membrane can be used to encase the absorbent materials. The attractant components can be dispensed from containers with either a semi-permeable top or a sealed top containing one or more holes to allow diffusion into the surrounding atmosphere. For example, the top can be pierced or punctured at the point of use to allow diffusion into the surrounding atmosphere. Suitable tops include, for example, metal foils (e.g., aluminum foil). The metal foil top can be sealed to an open top of a suitable attractant container, such as a polymer vial (e.g., PETG vial).

An alternative preferred embodiment involves the attractant Octenal or Hexenal; with or without the use of butyric acid as a co-attractant.

The following examples further illustrate the present invention and include protocols for the evaluation of the method of the present invention but, of course, should not be construed as in any way limiting its scope.

EXAMPLES

Example 1

A test mixture of 16.5 grams (0.196 mole) of sodium bicarbonate, 13.5 grams (0.064 mole) of citric acid monohydrate, and 2.0 gram (0.0098 mole) of magnesium chloride hexahydrate was placed into a 50 mL plastic centrifuge tube (Corning® 50 mL polypropylene centrifuge tubes), the centrifuge tube was capped and the contents shaken until a homogenous mixture was obtained (32 gram test mixture, a molar ratio of the effervescent agent to solid acid to deliquescent agent is 20:6.5:1). An 8.375 gram test mixture was prepared using 4.125 grams (0.0491 mole) of sodium bicarbonate, 3.75 grams (0.0178 mole) of citric acid monohydrate and 0.5 gram (0.0025 mole) of magnesium chloride hexahydrate (a molar ratio of the effervescent agent to solid acid to deliquescent agent is 20:7:1). A 16.0 gram test mixture was prepared using 8.25 grams (0.0982 mole) of sodium bicarbonate, 6.75 grams (0.0321 mole) of citric acid monohydrate and 1.0 gram (0.0049 mole) of magnesium chloride hexahydrate (a molar ratio of the effervescent agent to solid acid to deliquescent agent is 20:6.5:1). Each centrifuge tube was placed into a tube rack inside a clear plastic glove box. The glove box was maintained at a relative humidity of 11%, 50%, 75% or 100%. Each centrifuge tube was uncapped and the flow of carbon dioxide was measured by replacing the cap with a modified cap which had a hole into which a plastic pipette tip was securely inserted. One end of a plastic tube was affixed to the protruding pipette tip and the other end of the tube was affixed to a Resteck Corporation Electronic flow calibrator (Model 21606). After about one minute, the flow of carbon dioxide was recorded in mL/minute. Each tube was uncapped until the next flow measurement was recorded. A control test mixture containing 3.75 grams (0.0178 mole) of citric acid monohydrate, 4.125 grams (0.0491 mole) of sodium bicarbonate and no magnesium chloride hexahydrate was also tested. The experiments were run in triplicate and the average flow measurements are summarized in Table 1 below. A flow of 0.5 mL/minute or greater is considered an adequate flow for attracting bed bugs.

TABLE 1

| Carbon Dioxide Generation | | | | | | | | | |
|---|---|---|---|---|---|---|---|---|---|
| Test Mixture | Flow measurement (mL/min) at 11% Humidity | | | | | | | | |
| | 0 Hr | 1 Hr | 2 Hr | 3 Hr | 4 Hr | 7 Hr | 11 Hr | 15 Hr | 24 Hr |
| Control | 0.2 | 0.2 | 0.2 | 0.1 | 0.1 | 0.2 | 0.2 | 0.2 | 0.2 |
| 8.375 gram | 0.9 | 0.6 | 0.4 | 0.5 | 0.5 | 0.4 | 0.6 | 0.3 | 0.3 |
| 16.0 gram | 0.9 | 0.8 | 0.9 | 0.7 | 1.0 | 0.6 | 1.8 | 1.0 | 0.3 |
| 32.0 gram | 1.6 | 1.3 | 1.3 | 1.4 | 2.0 | 1.7 | 3.5 | 1.9 | 0.3 |
| Test Mixture | Flow measurement (mL/min) at 50% Humidity | | | | | | | | |
| | 0 Hr | 1 Hr | 2 Hr | 3 Hr | 4 Hr | 5 Hr | 7 Hr | 11 Hr | 15 Hr | 27 Hr |
| Control | 0.4 | 0.3 | 0.3 | 0.2 | 0.2 | 0.2 | 0.4 | 1.6 | 0.4 | 0.3 |
| 8.375 gram | 0.7 | 0.7 | 0.8 | 0.7 | 0.7 | 0.6 | 0.5 | 0.9 | 0.6 | 0.3 |
| 16.0 gram | 1.1 | 1.1 | 1.0 | 1.6 | 1. | 1.0 | 0.9 | 2.1 | 1.1 | 0.3 |
| 32.0 gram | 1.6 | 1.6 | 1.3 | 1.9 | 2.6 | 2.2 | 1.7 | 3.4 | 1.4 | 0.3 |
| Test Mixture | Flow measurement (mL/min) at 75% Humidity | | | | | | | | |
| | 0 Hr | 1 Hr | 2 Hr | 3 Hr | 4 Hr | 5 Hr | 7 Hr | 14 Hr | 23 Hr |
| Control | 0.5 | 0.5 | 0.6 | 0.5 | 1.7 | 2.2 | 1.2 | 0.2 | 0.2 |
| 8.375 gram | 0.9 | 0.9 | 1.1 | 0.9 | 0.9 | 1.0 | 0.9 | 0.8 | 0.3 |
| 16.0 gram | 1.1 | 1.1 | 1.3 | 1.5 | 1.3 | ND | 1.4 | 1.4 | 0.5 |
| 32.0 gram | 1.4 | 1.7 | 1.8 | 2.8 | 4.0 | ND | 2.7 | 2.2 | 1.0 |
| Test Mixture | Flow measurement (mL/min) at 100% Humidity | | | | | | | | |
| | 0 Hr | 1 Hr | 2 Hr | 3 Hr | 4 Hr | 8 Hr | 12 Hr | 24 Hr |
| Control | 0.3 | 1.0 | 1.6 | 2.0 | 2.2 | 0.3 | 0.2 | 0.1 |
| 8.375 gram | 0.8 | 1.2 | 1.2 | 1.2 | 1.2 | 1.1 | 1.5 | 0.2 |

TABLE 1-continued

| Carbon Dioxide Generation | | | | | | | | |
|---|---|---|---|---|---|---|---|---|
| 16.0 gram | 1.0 | 1.7 | 1.8 | 1.8 | 2.0 | 1.4 | 1.8 | 0.2 |
| 32.0 gram | 1.6 | 2.4 | 2.5 | 2.9 | 2.5 | 3.4 | 3.4 | 0.5 |

As can be seen from Table 1, an adequate flow of carbon dioxide is generated for a period of over 11 hours using a mixture of citric acid monohydrate, sodium bicarbonate and magnesium chloride hexahydrate without the addition of water when the relative humidity is at least 11%. The 32.0 gram test mixture can provide an adequate flow of carbon dioxide for up to 24 hours.

Example 2

Test mixtures of the following were prepared: 13.5 grams (0.064 mole) of citric acid monohydrate, 16.5 grams (0.196 mole) of sodium bicarbonate and either (1) 0.25 gram (0.00123 mole), (2) 0.5 (0.0025 mole), (3) 1.0 (0.0049 mole), (4) 2.0 (0.0098 mole), (5) 3.0 (0.0147 mole) or (6) 4.0 grams (0.0197 mole) of magnesium chloride hexahydrate or (7) 2.0 grams (0.0078 mole) of magnesium nitrate hexahydrate. The molar ratio of the effervescent agent to solid acid to deliquescent agent for each test mixture is as follows:
 (1) 159:52:1
 (2) 78:26:1
 (3) 40:13:1
 (4) 20:6.5:1
 (5) 13:4:1
 (6) 10:3:1
 (7) 25:8:1

Each mixture was placed into separate 50 mL plastic centrifuge tubes (Corning® 50 mL polypropylene centrifuge tubes), each centrifuge tube was capped and the contents shaken until a homogenous mixture was obtained. Each centrifuge tube was placed into a tube rack inside a clear plastic glove box. The glove box was maintained at a relative humidity of 50%. Each centrifuge tube was uncapped and the flow of carbon dioxide was measured by replacing the cap with a modified cap which had a hole into which a plastic pipette tip was securely inserted. One end of a plastic tube was affixed to the protruding pipette tip and the other end of the tube was affixed to a Resteck Corporation Electronic flow calibrator (Model 21606). After about one minute, the flow of carbon dioxide was recorded in mL/minute. Each tube was uncapped until the next flow measurement was recorded. The experiments were run in triplicate and the average flow measurements are summarized in Table 2 below. A flow of 0.5 mL/minute or greater is considered an adequate flow for attracting bed bugs.

As can be seen from Table 2, an adequate flow of carbon dioxide is generated for periods of up to 16 hours using a mixture of sodium bicarbonate, citric acid monohydrate and magnesium chloride hexahydrate without the addition of water having molar ratio of the effervescent agent to solid acid to deliquescent agent of from 159:52:1 to 10:3:1. The preferred molar ratio of the effervescent agent to solid acid to deliquescent agent of from 40:13:1 to 20:6.5:1 can provide an adequate flow of carbon dioxide for up to 24 hours. By changing the molar ratios of the agents the reaction kinetics are altered to generate carbon dioxide faster or slower.

Example 3

Into a room controlled at 50% humidity and about 70° F., was placed a plastic children's pool (POLY POOL by General Foam Plastics Corporation, Norfolk Va.) which was lined with brown kraft paper to provide a suitable walking surface for bed bugs, using masking tape to hold the paper in place. Twenty five bed bugs were placed into a paper cup that contained a four inch by four inch piece of flannel cloth as a harborage. The cup was capped, pin holes in the cap provided air for the bed bugs, and held for two hours, then was placed in the pool and allowed to acclimate. After about three hours the flannel harborage was transferred from the paper cup into the pool, about ten inches from the side.

A bed bug monitor and/or capture device was prepared by cutting two 4 inch by 4 inch pieces of chipboard and one 4 inch by 4 inch piece of fluted cardboard. The fluted cardboard was sandwiched between the chipboards and the unit was stapled on two sides to hold the unit together, creating a base segment (first piece of chipboard) an interior segment (fluted cardboard) and a top segment (second piece of chipboard). Two 50 mL plastic centrifuge tubes (Corning® 50 mL polypropylene centrifuge tubes) were taped to the top segment chipboard, with the fluting running vertical.

Ampoules were constructed employing a cylindrical outer shell made of polyethylene, and having a height of 14.5 mm and a diameter of 11 mm. One of these outer shells was filled

TABLE 2

| Carbon Dioxide Generation | | | | | | | | | | | | | | | |
|---|---|---|---|---|---|---|---|---|---|---|---|---|---|---|---|
| Test | Flow measurement (mL/min) at 50% Humidity | | | | | | | | | | | | | | |
| Mixture | 0 Hr | 1 Hr | 2 Hr | 3 Hr | 4 Hr | 5 Hr | 7 Hr | 9 Hr | 11 Hr | 14 Hr | 16 Hr | 21 Hr | 24 Hr | 26 Hr | 30 Hr |
| (1) | 0.5 | 0.4 | 0.5 | 0.9 | 1.0 | 0.3 | 0.3 | 0.5 | 2.6 | 1.3 | 0.9 | 0.2 | 0.1 | 0.1 | 0 |
| (2) | 1.0 | 0.8 | 1.1 | 2.0 | 1.6 | 0.7 | 0.7 | 0.8 | 4.4 | 1.4 | 1.2 | 1.3 | 0.2 | 0.1 | 0 |
| (3) | 1.2 | 1.1 | 0.9 | 1.8 | 1.6 | 1.0 | 0.8 | 0.9 | 1.3 | 0.9 | 0.9 | 1.0 | 0.7 | 0.2 | 0.1 |
| (4) | 1.8 | 1.3 | 1.2 | 1.3 | 1.2 | 1.4 | 1.3 | 1.2 | 0.7 | 0.8 | 0.5 | 0.4 | 0.7 | 0.4 | 0.3 |
| (5) | 2.0 | 1.4 | 1.5 | 1.4 | 0.9 | 0.8 | 0.7 | 1.5 | 1.5 | 0.9 | 0.7 | 0.4 | 0.3 | 0.1 | 0.2 |
| (6) | 2.1 | 1.3 | 1.4 | 1.5 | 1.2 | 0.85 | 0.6 | 0.6 | 0.3 | 0.9 | 1.9 | 0.7 | 0.1 | 0 | 0 |
| (7) | 1.4 | 2.9 | 1.8 | 1.6 | 1.1 | 0.8 | 1.1 | 3.5 | 1.3 | 0.8 | 0.6 | 0.9 | 0.9 | 0.5 | 0.3 | with a solution containing 2.535 milligrams of Octenal in 300 microliters of nonane. A cylindrical porous diffusion member, made of ultra high molecular weight polyethylene, was disposed inside the outer shell in a contraposition such that the volatile liquid was contained in the interior reservoir formed by such diffusion member. The opening of the outer shell was then thermally sealed with an aluminum film member, leaving a head space of about 2-2.5 mm between the bottom portion of the diffusion member and the top of the diffusion member. A hole having a diameter of about 0.23 mm was made in the aluminum film by puncturing it with a needle. A second ampoule containing 71.85 micrograms of butyric acid in 300 microliters of nonane was prepared in a similar manner as described above. The ampoules containing attractants Ocetenal and butyric acid were taped to the top of the device in a horizontal manner.

A mixture of 13.5 grams of citric acid monohydrate, 16.5 grams of sodium bicarbonate and 2.0 grams of magnesium chloride hexahydrate was placed into a separate container, the container was capped and the contents shaken until a homogenous mixture was obtained. This chemical mixture was divided equally between the two 50 mL plastic centrifuge tubes.

The bed bug monitor and/or capture device was attached to the back side of an "L" shaped wooden stand using plastic push pins. The wooden stand was made by vertically attaching a 10 inch by 10 inch piece of pine lumber to a base piece of 10 inch by two and a half inch piece of pine lumber. The back surface of the 10 inch by 10 inch vertical "L" shaped frame was roughened employing 100 grit sandpaper. The "L" shaped frame with the attractants affixed was placed in the children's pool about 24 inches from the flannel harborage. A weight was placed on the base piece to prevent the "L" shaped frame from tipping over. After 17 to 18 hours the device was removed and the number of bed bugs in the device, including those that fell into the open 50 mL centrifuge tubes, was counted. The test was repeated several times. Control tests using devices containing no attractants (bed bugs were released from inverted Petri dish cover after acclimation period) and tests using devices that contained only Octenal and butyric acid were also tested in the same manner as described above. The average number of bed bugs found in the devices is summarized in Table 3 below.

TABLE 3

Bed Bugs Caught In Vertical Test Devices

| Number of Replicates | Octenal and Butyric Acid Attractant Used | Carbon Dioxide Used | Average % Bed Bugs Found in Device |
| --- | --- | --- | --- |
| 7 | None | None | 17 |
| 5 | Yes | None | 20 |
| 12 | Yes | Yes | 38 |

What is claimed is:

1. A chemical composition for generating carbon dioxide for use with an insect monitor and/or capture device comprising:
   i) an effervescent agent,
   ii) a solid acid;
   iii) a deliquescent agent which is magnesium chloride hexahydrate, and optionally
   iv) an anti-clumping agent
      wherein the molar ratio of the effervescent agent to solid acid to deliquescent agent is from 159:52:1 to 10:3:1.

2. The composition of claim 1, wherein the effervescent agent comprises sodium bicarbonate.

3. The composition of claim 1, wherein the solid acid comprises citric acid monohydrate.

4. The composition of claim 1, wherein the anti-clumping agent comprises a material selected from the group consisting of fumed silica, amorphous silica, kaolin clay and mixtures thereof.

5. The composition of claim 1, wherein the molar ratio of the effervescent agent to solid acid to deliquescent agent of from 40:13:1 to 20:6.5:1.

6. A chemical composition for generating carbon dioxide for use with an insect monitor and/or capture device comprising:
   i) sodium bicarbonate,
   ii) citric acid monohydrate;
   iii) magnesium chloride hexahydrate, and optionally
   iv) an anti-clumping agent
      wherein the molar ratio of the sodium bicarbonate to citric acid monohydrate to magnesium chloride hexahydrate is from 159:52:1 to 10:3:1.

7. The composition of claim 6, wherein the molar ratio of sodium bicarbonate to citric acid monohydrate to magnesium chloride hexahydrate is from 40:13:1 to 20:6.5:1.

8. The composition of claim 1 wherein the solid acid is malic acid.

* * * * *